US008865477B2

(12) United States Patent
Shih et al.

(10) Patent No.: US 8,865,477 B2
(45) Date of Patent: Oct. 21, 2014

(54) WATER SOLUBLE NANOCRYSTALLINE QUANTUM DOTS CAPABLE OF NEAR INFRARED EMISSIONS

(75) Inventors: Wei-Heng Shih, Bryn Mawr, PA (US); Wan Y. Shih, Bryn Mawr, PA (US); Hui Li, Newark, DE (US); Ian McDonald, Weatherly, PA (US); Andrew Kopek, Chagrin Falls, OH (US); Ryan O'Malley, Norristown, PA (US); Yu-Chieh Lu, Hsinchu (TW)

(73) Assignee: Drexel University, Philadelphia, PA (US)

( * ) Notice: Subject to any disclaimer, the term of this patent is extended or adjusted under 35 U.S.C. 154(b) by 715 days.

(21) Appl. No.: 12/428,000

(22) Filed: Apr. 22, 2009

(65) Prior Publication Data

US 2009/0286257 A1    Nov. 19, 2009

Related U.S. Application Data

(60) Provisional application No. 61/046,899, filed on Apr. 22, 2008.

(51) Int. Cl.
| | |
|---|---|
| *C01B 17/20* | (2006.01) |
| *C01G 21/21* | (2006.01) |
| *C01G 11/02* | (2006.01) |
| *G01N 33/532* | (2006.01) |
| *B82Y 15/00* | (2011.01) |
| *G01N 33/58* | (2006.01) |
| *B82Y 5/00* | (2011.01) |
| *G01N 33/53* | (2006.01) |

(52) U.S. Cl.
CPC ............ *G01N 33/588* (2013.01); *G01N 33/532* (2013.01); *B82Y 15/00* (2013.01); *B82Y 5/00* (2013.01); *Y10S 977/774* (2013.01)
USPC .............. 436/523; 252/301.4 R; 252/301.4 S; 252/301.6 R; 252/301.6 S; 435/7.1; 423/561.1; 423/566.1; 977/774

(58) Field of Classification Search
None
See application file for complete search history.

(56) References Cited

U.S. PATENT DOCUMENTS

| 7,335,345 B2 * | 2/2008 | Shih et al. .................. 423/561.1 |
| 7,597,870 B2 * | 10/2009 | Shih et al. .................. 423/561.1 |
| 7,778,296 B1 * | 8/2010 | Vuckovic et al. ............... 372/41 |
| 7,824,653 B2 * | 11/2010 | Shih et al. .................. 423/561.1 |
| 8,080,229 B2 * | 12/2011 | Shih et al. .................. 423/561.1 |
| 2003/0030067 A1 * | 2/2003 | Chen ............................. 257/102 |
| 2004/0110002 A1 * | 6/2004 | Kim et al. ..................... 428/379 |
| 2006/0078490 A1 * | 4/2006 | Shih et al. .................. 423/566.1 |
| 2008/0057311 A1 | 3/2008 | Hollingsworth et al. |
| 2008/0107590 A1 | 5/2008 | Shih et al. |
| 2009/0065742 A1 | 3/2009 | Shih et al. |

FOREIGN PATENT DOCUMENTS

WO    2005067485 A2    7/2005

OTHER PUBLICATIONS

Pentia et al., "Structural, Electrical, and Photoelectrical Properties of CdxPb1-xS Thin Films Prepared by Chemical Bath Deposition," J. Electrochem. Society, 2004, vol. 151, Issue: 11, pp. G729-G733.*
U.S. Appl. No. 60/799,768, filed May 12, 2006.*
Aswathy et al., "Near-infrared quantum dots for deep tissue imaging," Anal. Bioanal. Chem., 2010, vol. 397, issue 4, pp. 1417-1435.*
Bruchez Jr. et al., "Semiconductor Nanocrystals as Fluorescent Biological Labels," Science, 1998, vol. 281, No. 5385, pp. 2013-2016.*
Zimmer et al., "Size Series of Small Indium Arsenide—Zinc Selenide Core-Shell Nanocrystals and Their Application to In Vivo Imaging," J. Am. Chem. Soc., 2006, 128 (8), pp. 2526-2527.*
Enustun, et al., "Physical and Inorganic Chemistry", Journal of the American Chemical Society, vol. 85, No. 21, Nov. 1963, pp. 3317-3328.
Chow, et al., "Gold Sol Formation Mechanisms: Role of Colloidal Stability", Journal of Colloid and Interface Science, 165, pp. 97-109, (1994).
Penn, et al., "Nanoparticles for Bioanalysis", Current Opinion in Chemical Biology, 2003, 7, pp. 609-615.
Brongersma, Mark L., "Nanoshells: Gifts in a Gold Wrapper", Nature Materials, vol. 2., May 2003, pp. 296-297.
Seydel, Caroline, "Quantum Dots Get Wet", Science, vol. 300, Apr. 4, 2003, pp. 80-81, www.sciencemag.org.

* cited by examiner

*Primary Examiner* — Galina Yakovleva
(74) *Attorney, Agent, or Firm* — Mendelsohn, Drucker & Dunleavy, P.C.

(57) ABSTRACT

A novel quantum dot capable of near infrared emissions at wavelengths of 750-1100 is made by forming solid solutions of metal sulfide, metal selenide or metal sulfide selenide by incorporating a suitable amount of an additional metallic element or elements to provide an emission wavelength in the range of 750 nm to 1100 nm. The quantum dots may be enabled for bioconjugation and may be used in a method for tissue imaging and analyte detection.

14 Claims, 8 Drawing Sheets

US 8,865,477 B2

WATER SOLUBLE NANOCRYSTALLINE QUANTUM DOTS CAPABLE OF NEAR INFRARED EMISSIONS

STATEMENT OF GOVERNMENTAL INTEREST

This invention was made with government support under Contract No. R01 EB000720 awarded by the National Institutes of Health. The Government has certain rights in the invention.

BACKGROUND OF THE INVENTION

1. Field of Invention

The present invention is directed to photoluminescent semiconductor nanocrystals and a method for enhanced biological imaging and analyte detection using near-infrared emissions.

2. Brief Description of the Prior Art

Semiconductor nanocrystals, hereinafter referred to as quantum dots (QDs), with surface bioconjugates have been studied extensively because of their unique optical properties. QDs are inorganic nanoparticles that emit light at a specific wavelength when excited. When light impinges on the QDs, electrons in the valence band are excited to the conduction band, forming short-lived (nanoseconds) electron-hole pairs called excitons that emit photons of a specific wavelength when the electron-hole pairs eventually recombine. The excitonic emission is not as dependent on the excitation light wavelength as that of fluorescent molecules. Therefore it is easier to excite QDs to luminescence than to excite traditional fluorescent molecules that require a specific excitation wavelength. The wavelength of the emitted photons of QDs, however, is specific to and controlled by the composition of the QDs and defect states inside the energy gap.

In the last few years, the interest in using QDs in biomedical imaging has exploded due to advances in surface modification of QDs that have made them accessible for antibody immobilization and detection of antibody-antigen binding. QDs may be used as imaging markers inside living organisms and may also be used as biological markers to find a disease as well as to carry a drug to the exact cell that needs it by immobilizing antibodies on the surface of the QDs. QDs may be specific to a particular disease and may be tailored to bind only to infected cells. Detection may be carried out either by locating the QDs' particles or by detecting signals emanating from the QDs' particles. For example, luminescence of antibody-coated QDs bound to the cancerous tissue in a mouse helped to locate a tumor (Quantum Dots Get Wet, *Science*, volume 300, p.80, Apr. 4, 2003). Until now the main biological tags that have been employed are organic fluorophores or radioactive labels (S. G. Penn, L. He, and M. J. Natan, "Nanoparticles for Bioanalysis", *Curr. Opin. Chem. Bio.*, 7, 1-7, (2003)). Radioactive labels are short lived and radioactive. Concerns about the use of radioactive materials in the body always arise. Organic fluorophores have wide emission spectra and the emission is not as bright as that of QDs. In comparison to conventional dye molecules, QDs have the advantages of having tunable fluorescence signatures, narrow emission spectra, brighter emissions, and good photostability (M. L. Brongersma, "Nanoshells, "Gifts in a Gold Wrapper", *Nature Materials*, vol. 2, May 2003.). The fabrication process of water-soluble luminescent QDs, however, is prohibitively expensive and complex, typically requiring the elimination of QD broadband emissions, thus compromising the commercializability of the QDs.

Recently, there has been a significant amount of interest in developing effective near infrared (NIR) emission QDs that enable deep tissue imaging, such as is addressed, for example, in U.S. Patent Publication No. 20080039816. Notably, these quantum dots may be fabricated from a wide variety of materials including CdS. Other references such as U.S. Patent Publication 2008/0057311 also disclose QDs fabricated from nanocrystalline materials, such as CdS and PbS. These references, however, do not appear to disclose a lead cadmium compound QD, such as $Cd_{1-x}Pb_xS$, that is capable of NIR emission. Thus, there remains a need to develop highly luminescent QDs capable of producing a near-infrared emission without expressing undesirable broadband emissions.

SUMMARY OF THE INVENTION

In one aspect, the present invention is directed to a quantum dot composition which is capable of NIR emission. The quantum dot is based on, for example, cadmium or zinc and may be a sulfide or selenide. The quantum dot may contain a sufficient amount of a suitable long-wavelength emitting component to ensure that the quantum dot is capable of a NIR emission at a wavelength of at least 750 nm.

In a second aspect of the invention, the invention is directed to a method for using a quantum dot involving the step of providing a quantum dot that is capable of NIR emission, binding a receptor to said quantum dot, binding the receptor to a target moiety and exciting said quantum dot such that it produces near infrared emissions.

In a third aspect, the invention is directed to a method for tuning the emission spectrum of a quantum dot by shifting the emission peak of the quantum dot to within the near infrared wavelength range by adding a suitable amount of a component to shift the emission of the quantum dot to a wavelength of from 750 nm to 1100 nm.

DETAILED DESCRIPTION OF THE PREFERRED EMBODIMENTS

Figure 1:
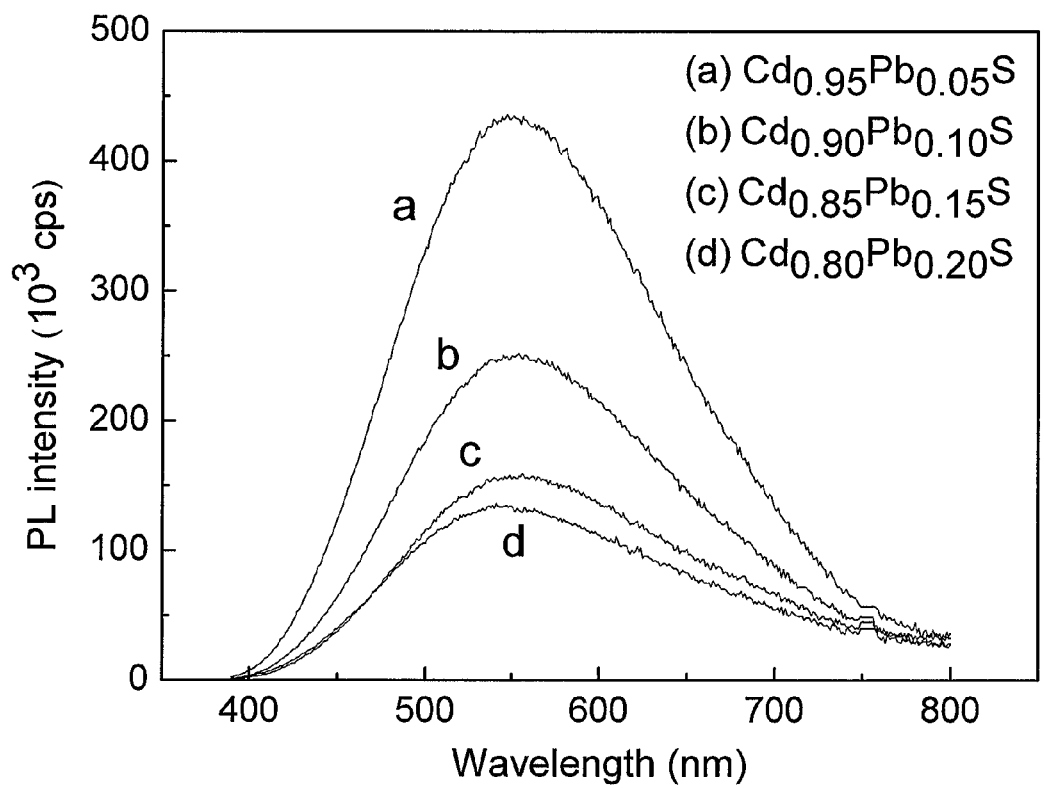
FIG. 1 shows emission spectra for $Cd_{0.95}Pb_{0.05}S$, $Cd_{0.90}Pb_{0.10}S$, $Cd_{0.85}Pb_{0.15}S$, $Cd_{0.80}Pb_{0.20}S$ QD colloids excited at 375 nm.

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

It must be noted that as used herein and in the appended claims, the singular forms "a", "an", and "the" include plural references unless the context clearly dictates otherwise. Thus, for example, reference to "a quantum dot" includes a plurality of quantum dots and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

The present invention pertains to a novel water-soluble and highly luminescent quantum dot (QD) composition enabled for bioconjugation and capable of near-infrared (NIR) emission and method for making such QDs. The invention is further directed to a novel method for enhancing biological imaging and analyte detection using the NIR emissions of the QD. It is envisioned that the present invention may be used to enhance deep tissue imaging, telecommunications, solar cells, photovoltaics, energy harvesting and infrared sensing and imaging technologies.

The QD of the present invention may be composed of any nanocrystalline material capable of producing emissions in the NIR spectrum, which is considered to encompass wavelengths from 750 to 1100 nm. More preferably, the emission wavelength of the QDs is from about 775 to about 900 nm, and most preferably, from about 800 to 875 nm.

It is preferred to have excitation wavelengths up to about 1100 nm. However, excitation wavelengths of 300-1100 nm may be employed and more preferably, excitation wavelengths of 350-800 nm are employed.

The QD composition may have a compositional formula $D_xM_{(1-x)}Se_yS_{(1-y)}$, where M is a metal element, D is at least one additional element or dopant selected from zinc, cadmium, lead, mercury, iron, manganese and mixtures thereof, S represents sulfide, Se represents selenide, and x and y define the molar concentrations of the various components. Exemplary metal components (M) for use in the present invention may include cadmium, zinc and mixtures thereof. X and y may be independently selected and are within the range of 0-1. In an exemplary embodiment, x may be larger than 0 and is selected to provide a QD having an emission having a wavelength of from about 750 nm to about 1100 nm. Depending on the particular (M) and (D) employed, x may range from 0-1, more preferably, from 0.25-0.85 and most preferably, from 0.4-0.8.

In an exemplary embodiment, the QD composition includes at least two metal compounds and is preferably a metal sulfide (MS), a metal selenide (MSe), or a metal sulfide selenide (MSSe) that contains at least one additional element or dopant (D) selected from zinc, cadmium, lead, mercury, iron, manganese and mixtures thereof, except that the additional element or dopant (D) is not zinc when (M) is zinc and is not cadmium when (M) is cadmium. In an exemplary embodiment, the molar ratio of the dopant (D) to the metal components (M) may be from about 60:40 to about 100:0, preferably, from about 60:40 to about 90:10, more preferably, about 60:40 to about 80:20 and most preferably, about 60:40 to about 70:30.

In another exemplary embodiment, the QD may have a composition including cadmium, lead and sulfide, such as $Pb_xCd_{(1-x)}S$, wherein x is at least 0.25, and more preferably ranges from 0.25-0.85, most preferably, from 0.4-0.8.

The composition of the QD may be determinative of the QD optical properties. The emission band width and NIR emission capability may be controlled by adjusting the composition of the quantum dot, e.g. by adjusting the amount or type of element or dopant, D, added to the QD composition. Specifically, the emission peak of a nanocrystalline material, such as CdS, can be shifted to above 750 nm by incorporating a sufficient amount of a long-wavelength emitting element or dopant, such as lead.

Capping molecules may be used in the current invention to limit the size, protect and stabilize the QDs. The capping molecules may also enable bioconjugation of molecules, such as antibodies, streptavidin, lectins, and nucleic acids to be coupled to the QD. Suitable capping molecules and methods of application are known to persons skilled in the art. In an exemplary embodiment, the capping molecules may be selected from carboxylated molecules, such as but not limited to mercaptocarboxylic acid (MCA) and 3-mercaptopropionic acid ($HSCH_2CH_2COOH$) (MPA), that enable surface immobilization of antibodies and other biomolecules.

In an exemplary embodiment, the molar ratio of (D and/or M):(S and/or Se) may be equal to or greater than 1. The quantum dots of the present invention may have molar ratios of the capping molecule:(D and/or M) of about 1:3 to about 8:1, preferably, from about 1:1 to about 2:3. Without wishing to be bound by theory, it is believed the molar ratio may influence the intensity of the photoluminescence of the final quantum dot.

Notably, the QDs of the present invention have the unique capability of excitonic photoluminescence in the wavelength range of 750-1100 nm. The capability of QDs to be excited for emission in this wavelength range renders them particularly effective and beneficial for imaging living tissue. The near infrared radiation of the QDs will pass through a sufficient depth of living tissue to enable non-invasive imaging of tissue conjugated to the biomolecules of the QDs.

The method of the present invention may involve use of the capability of the QDs to enhance tissue imaging and in situ analyte detection. The quantum dot of the present invention may be directly or indirectly conjugated to a receptor, such as a molecule or biological agent that specifically recognizes and binds to a target moiety, including any molecule, biological agent or receptor expressed on a population of cells. Target moieties may include, but are not limited to, antibodies, or fragments thereof, peptides, hormones, growth factors, cytokines, and any other naturally- or non-naturally-existing ligands, which bind to cell surface receptors. Upon excitation, the QD may generate NIR emissions enabling in situ analyte detection and/or deep tissue imaging. Notably, tissue imaging and analyte detection are enhanced when using NIR emissions because light separates from the major absorption peaks of hemoglobin and water, enabling a greater penetration depth than visible light in organs and tissues. It may be possible to enable noninvasive deep tissue imaging at a depth typical of NIR penetration, as well as at other depths well known to skilled persons.

Although the QDs of the present invention may be particularly beneficial for biological applications, such as biomarkers and deep tissue imaging, the QDs may also be useful for a wide variety of other applications, including improving optical properties and conductivity of telecommunication connections, solar and thermal photovoltaic devices as well as other energy harvesting devices and infrared sensing and imaging technologies.

The novel QDs of the present application may be fabricated by a three step process involving fabricating a QD from water-soluble precursors, capping the QD with carboxylated molecules and adding an excess amount of cation to the quantum dot core. It may also be possible to subsequently replace the carboxylated molecules with other molecules to enhance photoluminescence and stability of the QD. This aqueous process is effective in producing a substantially clean quantum dot surface enabling a high luminescence yield.

The aqueous synthesis of the QD begins with selecting a starting material that may be any salt of a metal suitable and soluble in water. Exemplary water-soluble metal salts that may be employed are metals that can form sulfides, such as $Cd(NO_3)_2$, $Cd(ClO_4)_2$, $CdCl_2$, $CdSO_4$, cadmium acetate, $Zn(NO_3)_2$, $Zn(ClO_4)_2$, $ZnSO_4$, $ZnCl_2$, zinc acetate, $Mn(NO_3)_2$, $Mn(ClO_4)_2$, $MnSO_4$, $MnCl_2$, manganese acetate, $Pb(NO_3)_2$, $Pb(ClO_4)_2$, $PbSO_4$, $PbCl_2$, and lead acetate.

Optionally, any thiol-functionalized molecule with a charged group, preferably on the opposite end, may be used as a capping molecule for reacting with the metal salt, as long as the thiol-functionalized molecule is water-soluble. Exemplary thiol-functionalized molecules include 4-aminothiophenol, mercaptosilanes such as 3-mercaptopropyltrimethoxysilane, and similar materials, as well as mercaptocarboxylic acids such as mercaptoacetic acid, mercaptopropionic acid, mercaptosuccinic acid, mercaptobenzoic acid, and mercaptoundecanoic acid. Any concentration of thiol-functionalized molecule may be employed, as long as it is within the solubility limit of the thiol-functionalized molecule in aqueous media.

The ratio of the various capping reactants may be varied in order to customize the particle size of the resultant capped QDs. In general, however, the molar ratio of thiol groups to metal may vary from about 1 to about 100, though ratios of 1-5 are more preferred, with a ratio of about 2 being most preferred. The fabricated highly luminescent QD may be capped with mercaptocarboxylic acids (MCA), preferably in a one step process. Alternatively, a capping molecule capable of chelating with the metal ions of the QD may be used to minimize the formation of impurity states due to dangling metal ions. These capping molecules may stabilize and limit the growth of the quantum dot particles. 3-mercaptopropionic acid ($HSCH_2CH_2COOH$) (MPA) is preferred as the capping molecule because it has a thiol group that can bind to various metal ions such as Cd. This follows the example of synthesizing monodispersed gold suspensions using sodium citrate (B. V. Enustun and J. Turkevich, "Coagulation of Colloidal Gold", *J. Am. Chem. Soc.*, 85, (21), 3317-3328, (1963), the disclosure of which is hereby incorporated by reference in its entirety.). Citrate not only reduces the gold but also serves as the capping molecule to stabilize the gold particles. By varying the ratio of citrate to gold, gold particle size is controlled (M. K. Chow and C. F. Zukoski, "Gold Sol Formation Mechanisms: Role of Colloidal Stability", *J. Colloid & Interf. Sci.*, 165, 97-109, (1994), the disclosure of which is hereby incorporated by reference in its entirety.). Without being bound by theory, MPA may play a similar role to cap and stabilize CdS QDs.

The one or more metal salt starting materials and one or more capping molecules may be reacted together to form an initial quantum dot solution. The solution may be prepared with deionized water or other suitable solvent. In an exemplary embodiment, the metal salt, in the form of a solution, may be quickly poured into the quantum dot solution. Alternatively, the metal salt solution may be added to the quantum dot solution at a controlled flow rate to prevent the quantum dot molecules from growing too large and potentially precipitating out of the solution during the fabrication process. In an exemplary embodiment, the metal salt component may be added over a period of from about 1 to about 20 minutes, preferably, about 10 to about 20 minutes and more preferably, about 10-15 minutes. Optionally, a dopant may also be added to the initial quantum dot solution. After mixing, one or more water-soluble sulfides and/or selenides may be added to the solution. Any suitable water-soluble sulfide and/or selenide may be used as a reactant in this method. Exemplary water-soluble sulfides that may be employed are sulfides such as $Na_2S$, $K_2S$. Also, sulfide gases, such as $H_2S$, may be bubbled through the aqueous solution. Generally, it is desirable to use about a stoichiometric amount of the sulfide and/or selenide. However, varying the amount of sulfide from a stoichiometric amount can, in some cases, produce desirable variations in the particle sizes of the QDs and thus, it may be useful to use anywhere from 0.1 to 10 times the stoichiometric amount of sulfide and/or selenide, more preferably 0.5 to 5 times the stoichiometric amount of the sulfide and/or selenide, and most preferably about 0.8-1.2 times the stoichiometric amount of the sulfide and/or selenide. The stoichiometric amount is based on the reaction of the sulfide and/or selenide with the metal to form the metal sulfide.

Upon mixing, quantum dots may precipitate from the solution turning the solution to a colloidal suspension. In an exemplary embodiment, when precipitation is complete, an additional amount of one or more cations may be added to the quantum dot suspension. The excess cations may be added to the quantum dot core within the suspension. Without wishing to be bound by theory, it is believed that the excess cations added to the quantum dot core may, in some cases, increase the intensity of the photoluminescence of the final quantum dot product and facilitate detection of luminescence from the quantum dot. In an exemplary embodiment, prior to the addition of the excess cation ions, the molar ratio of the capping molecule:(D and/or M):(S and/or Se) may be about 2:1:1 or about 2:2:1. After the addition of excess cation core, the molar ratio may be about 2:3:1. Thus, sufficient additional cations may be added to increase the molar ratio of cations to sulfide and/or selenide from about 1:1 up to about 4:1 or from about 2:1 up to about 4:1.

Occasionally, difficulties may arise during the quantum dot synthesis if the pH of the reaction mixture is in the vicinity of the isoelectric point (IEP) of the precipitating particles. Thus, in such cases, it may be desirable to adjust the pH of the reaction mixture away from the IEP of metal sulfide and/or selenide using a suitable, water-soluble pH-adjusting agent, before the addition of one or more water-soluble sulfides and/or selenides, such as sodium sulfide. Optionally, if additional cation is added, the pH may be adjusted after the addition of the excess cations.

One example of a suitable pH-adjusting agent is ammonium hydroxide. The concentration of the pH-adjusting agent may be varied, as necessary, to produce optimum results. Preferred concentrations of ammonium hydroxide are in the range of about 0.5-2 M and, more preferably, about 0.8-1.2 M, with about 1 M being the most preferred concentration of the ammonium hydroxide as the pH-adjusting agent.

After adjustment of the pH away from the IEP of the metal sulfide and/or selenide, the water-soluble sulfide and/or selenide, such as sodium sulfide, is added quickly to minimize the reaction time. A few minutes of reaction time is sufficient. The process is best performed in oxygen-free environment to avoid the photo-oxidation reaction of sulfur and/or selenium. To prevent further particle growth, the reacted solution is quenched to freezing point of water and then stored in refrigerator.

EXAMPLES

Example 1

Various different aqueous $Cd_{1-x}Pb_xS$ QD colloids were investigated to compare their NIR emission capabilities. In general, cadmium sulfide bulk has a band gap of about 2.4 eV, corresponding to a wavelength of about 517 nm. By contrast, PbS bulk has a band gap of about 0.37 eV, corresponding to a wavelength of about 3351 nm. By combining these elements, it is possible to create a near-infrared emission having a wavelength of at least about 750 nm.

In this experiment, QDs colloids of CdS, $Cd_{0.95}Pb_{0.05}S$, $Cd_{0.90}Pb_{0.10}S$, $Cd_{0.85}Pb_{0.15}S$, $Cd_{0.80}Pb_{0.20}S$, $Cd_{0.75}Pb_{0.25}S$, $Cd_{0.6}Pb_{0.4}S$, $Cd_{0.5}Pb_{0.5}S$, $Cd_{0.4}Pb_{0.6}S$, $Cd_{0.3}Pb_{0.7}S$ were synthesized according to the general method disclosed in Examples 2 and 3. Photoluminescence characterization showed that $Cd_{0.95}Pb_{0.05}S$, $Cd_{0.90}Pb_{0.10}S$, $Cd_{0.85}Pb_{0.15}S$, $Cd_{0.80}Pb_{0.20}S$ emitted visible light when excited by UV light at a wavelength of 375 nm as shown in FIG. 1.

Figure 2:
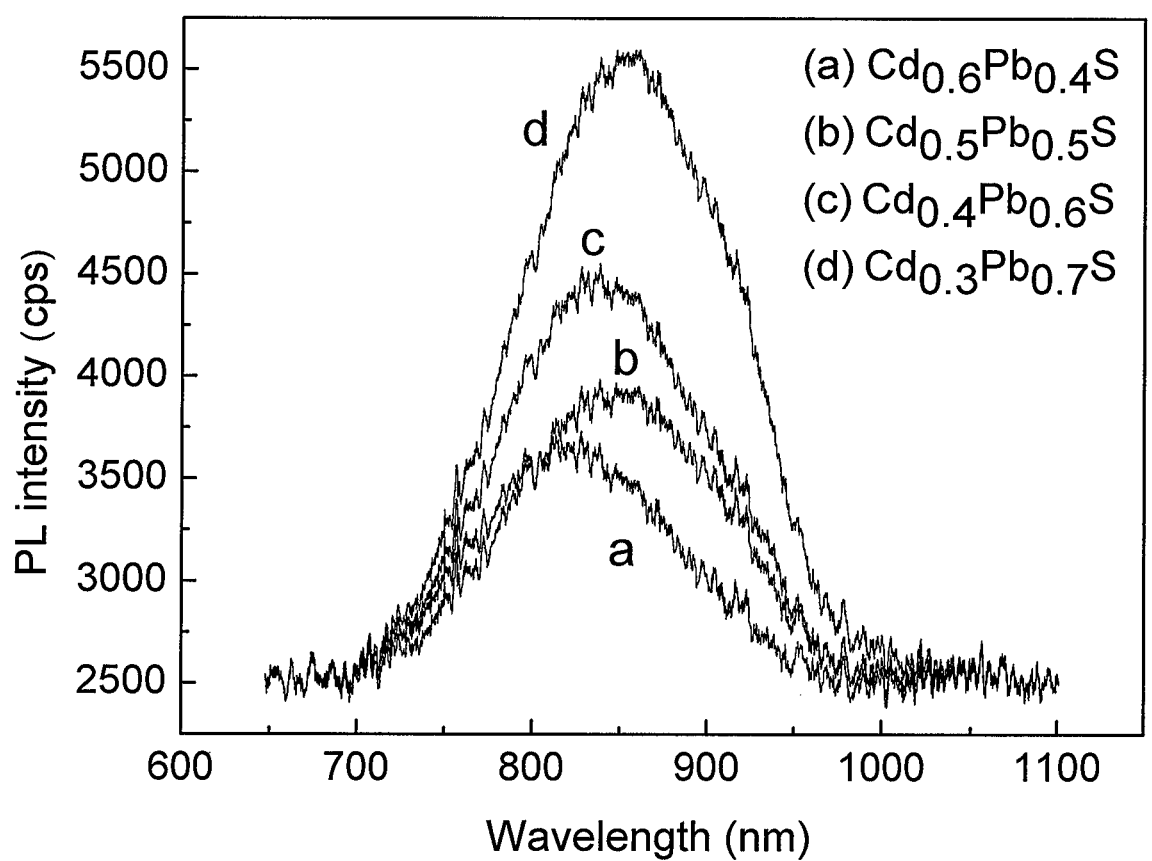
FIG. 2 shows emission spectra for $Cd_{0.6}Pb_{0.4}S$, $Cd_{0.5}Pb_{0.5}S$, $Cd_{0.4}Pb_{0.6}S$, $Cd_{0.3}Pb_{0.7}S$ QD colloids excited at 440-470 nm.

FIG. 2 shows the emission profile of high lead content QD colloids, $Cd_{0.6}Pb_{0.4}S$, $Cd_{0.5}Pb_{0.5}S$, $Cd_{0.4}Pb_{0.6}S$, $Cd_{0.3}Pb_{0.7}S$, when excited at 440-470 nm. Notably, $Cd_{0.3}Pb_{0.7}S$ in FIG. 2 shows a high peak emission at about 850 nm within the NIR range. FIGS. 1-2 clearly demonstrate that by varying the Pb content of $Cd_{1-x}Pb_xS$ to higher than 25% Pb, it is possible to induce NIR emission.

Example 2

An exemplary embodiment of the QD of the present invention is $Cd_{0.75}Pb_{0.25}S$, which was fabricated from cadmium nitrate $[Cd(NO_3)_2]$ (Alfa Aesar), lead nitrate $[Pb(NO_3)_2]$ (Fisher), sodium sulfide $[Na_2S]$ (Sigma Aldrich), 3-mercaptopropionic acid [MPA] (Sigma Aldrich), tetrapropylammonium hydroxide $[(CH_3CH_2CH_2)_4NOH]$, 1M (Sigma Aldrich), and deionized (DI) water.

The $Cd_{0.75}Pb_{0.25}S$ QDs was fabricated by a process of aqueous synthesis from metal sulfide precursors. Specifically, the method for synthesis involved preparing a 0.04 M $Cd(NO_3)_2$ solution in DI water, preparing a 0.04 M $Pb(NO_3)_2$ solution in DI water and preparing a 0.02 M $Na_2S$ solution in DI water. 0.16 mmol of MPA was then dissolved into 40 ml of DI water and subsequently stirred for 5 min to create the basis of the mixture for fabricating the QDs.

1.5 ml of the prepared $Cd(NO_3)_2$ solution was added to the MPA base solution, and the mixture was stirred for 5 min. Subsequently, 0.5 ml of the $Pb(NO_3)_2$ solution was added into the mixture of MPA and $Cd(NO_3)_2$, and the mixture was stirred for 10 min. $(CH_3CH_2CH_2)_4NOH$ was also added to the mixture until the pH of the mixture reached 7.7. 4 ml of the prepared $Na_2S$ solution was then quickly added to the mixture. The mixture was subsequently stirred for 5 min. 2 ml of the $Cd(NO_3)_2$ solution was then slowly added, and the mixture was stirred for 5 min. The resultant suspension formed a transparent yellow QD suspension characterized by a final pH of about 7.0, and was refrigerated and stored at 4° C. The concentration of the fabricated $Cd_{0.75}Pb_{0.25}S$ suspension was about 1.6 mM based on the concentration of S. The molar ratio MPA:(Cd+Pb):S for the fabricated quantum dots was 2:2:1.

Figure 3:
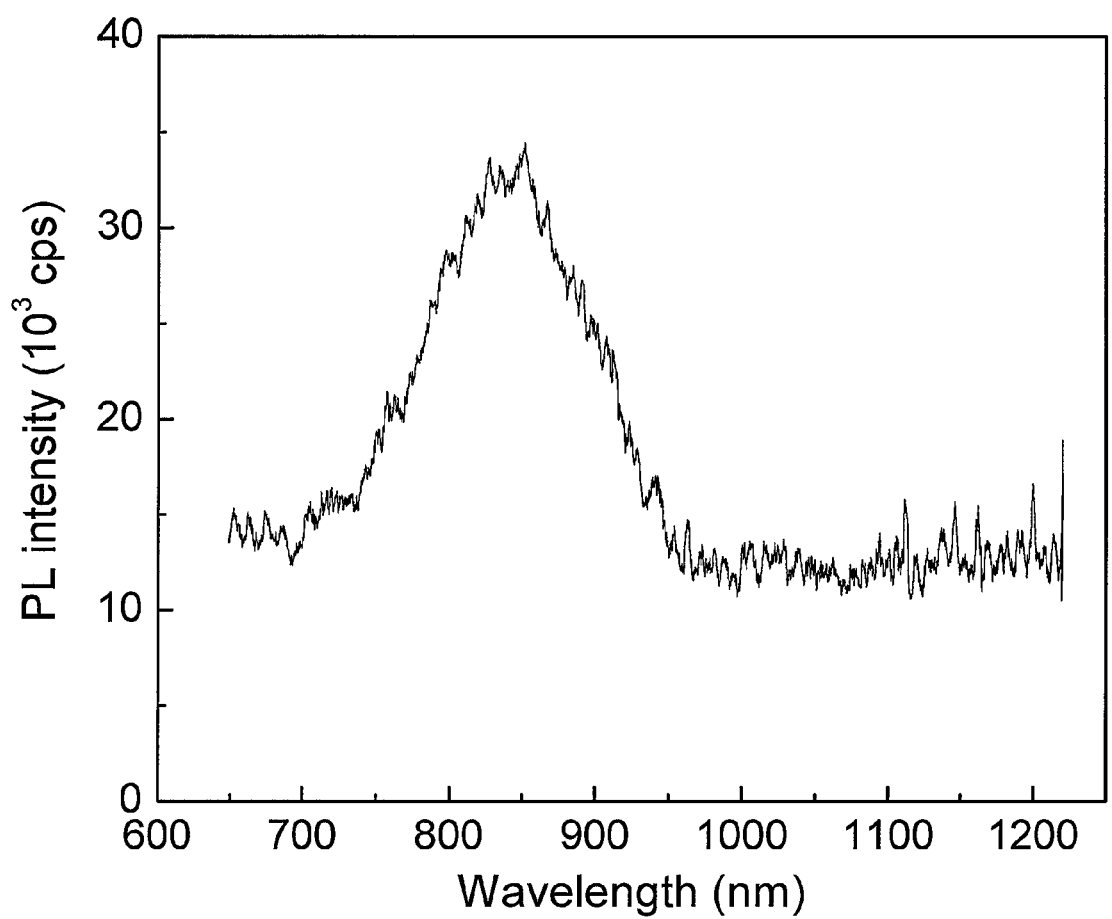
FIG. 3 is an emission spectrum for $Cd_{0.75}Pb_{0.25}S$ QDs excited at 425 nm.

Notably, the aqueous $Cd_{0.75}Pb_{0.25}S$ QDs fabricated from the $Cd_{0.75}Pb_{0.25}S$ suspension were photoluminescent. The optical properties of the fabricated QDs were subsequently investigated. As shown in FIG. 3, upon exciting the QDs at a wavelength of 425 nm, the QDs produced an emission of about 840 nm.

Example 3

Another exemplary embodiment of the QD of the present invention is $Cd_{0.5}Pb_{0.5}S$, which was fabricated from cadmium nitrate $[Cd(NO_3)_2]$ (Alfa Aesar), lead nitrate $[Pb(NO_3)_2]$ (Fisher), sodium sulfide $[Na_2S]$ (Sigma Aldrich), 3-mercaptopropionic acid [MPA] (Sigma Aldrich), tetrapropylammonium hydroxide $[(CH_3CH_2CH_2)_4NOH]$, 1M (Sigma Aldrich), and deionized (DI) water.

The $Cd_{0.5}Pb_{0.5}S$ QDs were fabricated by a process of aqueous synthesis from metal sulfide precursors. Specifically, the method for synthesis involved preparing a 0.04 M $Cd(NO_3)_2$ solution in DI water, preparing a 0.04 M $Pb(NO_3)_2$ solution in DI water and preparing a 0.02 M $Na_2S$ solution in DI water. 0.16 mmol of MPA was then dissolved into 38 ml of DI water and subsequently stirred for 5 min to create the basis of the mixture for fabricating the QDs.

1 ml of the prepared $Cd(NO_3)_2$ solution was added to the MPA base solution, and the mixture was stirred for 5 min. Subsequently, 1 ml of the $Pb(NO_3)_2$ solution was added into the mixture of MPA and $Cd(NO_3)_2$, and the mixture was stirred for 10 min. $(CH_3CH_2CH_2)_4NOH$ was also added to the mixture until the pH of the mixture reached 9. 4 ml of the prepared $Na_2S$ solution was then quickly added to the mixture. The mixture was subsequently stirred for 5 min. 4 ml of the $Cd(NO_3)_2$ solution was then slowly added, and the mixture was stirred for 5 min. More $(CH_3CH_2CH_2)_4NOH$ was then added until the suspension reached a pH value of 12. The resultant suspension was refrigerated and stored at 4° C.

Using the same above procedure, batches of $Cd_{1-x}Pb_xS$ QDs suspensions for 0.4<x<0.7 were prepared. All the resultant suspensions were transparent and exhibited a more yellow appearance with increasing x values. The final pH of all the suspensions was about 12, and the concentration was 1.6 mM based on the concentration of S. The molar ratio of MPA:(Cd+Pb):S for the fabricated QDs was 2:3:1, with excess Cd and varying Cd:Pb ratio.

The photoluminescence properties for the fabricated $Cd_{0.6}Pb_{0.4}S$, $Cd_{0.5}Pb_{0.5}S$, $Cd_{0.4}Pb_{0.6}S$, $Cd_{0.3}Pb_{0.7}S$ QDs suspensions were investigated, and the results are presented in Table 1.

TABLE 1

Optical Properties of $Cd_{0.6}Pb_{0.4}S$, $Cd_{0.5}Pb_{0.5}S$, $Cd_{0.4}Pb_{0.6}S$, $Cd_{0.3}Pb_{0.7}S$ QD Suspensions

| (1 − x)/x (Cd/Pb) ratio) | Excitation wavelength (nm) | $1^{st}$ emission peak | | | $2^{nd}$ emission peak | | |
|---|---|---|---|---|---|---|---|
| | | (nm) | (cps) | % | (nm) | (cps) | % |
| 0.6/0.4 | 440 | 811 | 1036.8 | 74.8 | 885 | 414.2 | 25.2 |
| 0.5/0.5 | 445 | 836 | 1247.0 | 84.8 | 905 | 381.6 | 15.2 |
| 0.4/0.6 | 470 | 835 | 1866.5 | 90.6 | 917 | 383.7 | 9.4 |
| 0.3/0.7 | 465 | 844 | 2778.0 | 88.4 | 914 | 732.8 | 11.6 |

As can be seen, though the emission spectra can be deconvoluted into two peaks, when the Pb component increased, generally both the optimal excitation wavelength and resultant emission peaks of the $Cd_{1-x}Pb_xS$ QDs suspensions shifted to longer wavelengths. The QDs with a larger amount of Pb exhibited higher emission intensity in the NIR range.

Example 4

Exemplary aqueous $Cd_{1-x}Pb_xS$ QDs were synthesized according to the following co-precipitation method at room temperature. The chemicals used to fabricate the quantum dots, $Cd(NO_3)_2$ (Fisher Scientific, USA), $Pb(NO_3)_2$ (Fisher Scientific, USA), $Na_2S$ (Sigma-Aldrich, USA), (MPA) (Sigma-Aldrich, USA) and tetrapropylammonium hydroxide solution (Alfa Aesar, Ward Hill, Mass.), were of analytical grade and did not undergo further purification. All solutions were prepared using deionized water (Millipore) as the solvent.

Figure 4:
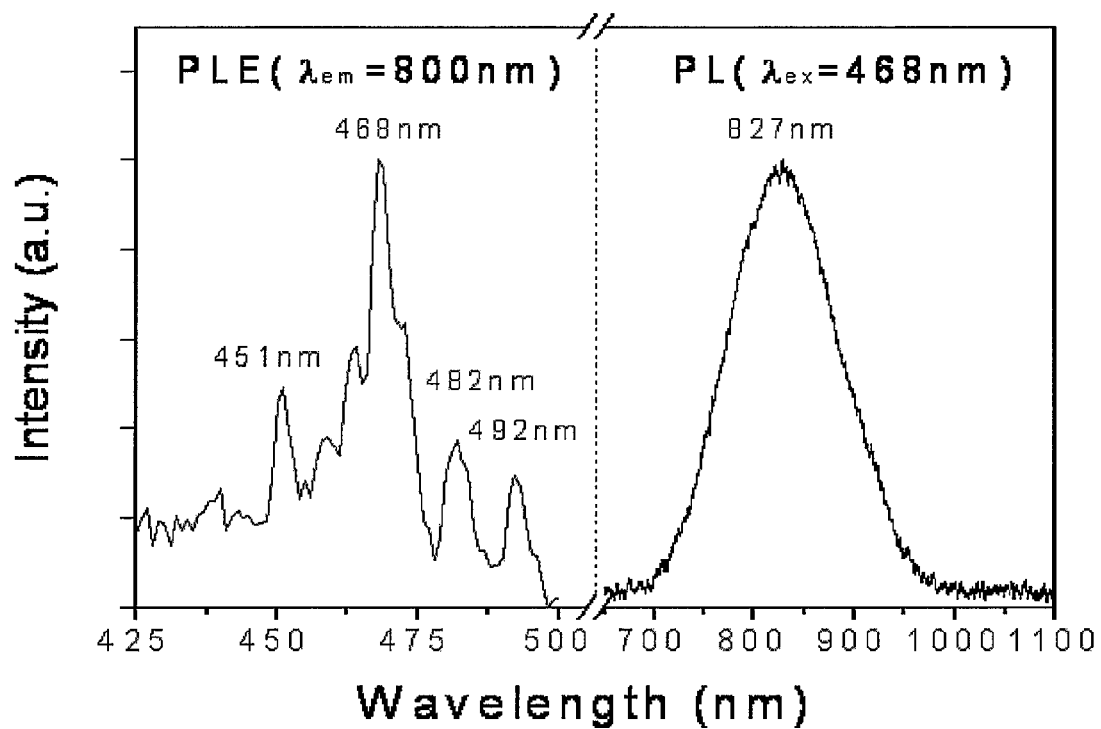
FIG. 4 is a photoluminescence excitation and emission spectra of $Cd_{0.3}Pb_{0.7}S$ QD with a MPA:(Cd+Pb):S molar ratio of about 2:2:0.375.

The process for synthesizing quantum dots, such as $Cd_{0.3}Pb_{0.7}S$, involved mixing 0.6 ml of 0.04 M $Cd(NO_3)_2$ and 1.4 ml of 0.04 M $Pb(NO_3)_2$ with the capping molecule 3-mercaptopropionic acid (MPA) in water while stirring. During mixing, the initially clear solution turned slightly pale, suggesting that certain lead salts precipitated out of the solution. The pH of the solution was then adjusted to 10.5 through the addition of a 1M tetrapropylammonium hydroxide solution. While stirring at ambient temperature, 0.75 ml of a 0.04 M $Na_2S$ precursor was instantly injected into the solution to obtain a CdPbS colloidal suspension. Precipitation of the suspension was completed after 10 min. An excess 2 ml of 0.04 M $Cd(NO_3)_2$ was then added until the pH of the suspension rose to about 12 and the cloudy solution eventually turned clear. The final QDs suspension had a MPA:(Cd+Pb):S compositional molar ratio of about 2:2:0.375, a volume of about 50 ml and a nominal $Cd_{0.3}Pb_{0.7}S$ concentration of about 0.6 mM. FIG. 4 is a fluorescence spectrum of the quantum dot, showing a well defined NIR emission peak at about 827 nm.

Example 5

Exemplary aqueous $Cd_{1-x}Pb_xS$ QDs were synthesized at ambient room temperature according to the following procedure. The chemicals used to fabricate the quantum dots, $Cd(NO_3)_2$ (Fisher Scientific, USA), $Pb(NO_3)_2$ (Fisher Scientific, USA), $Na_2S$ (Sigma-Aldrich, USA), MPA (3-mercaptopropionic acid) (Sigma-Aldrich, USA) and tetrapropylammonium hydroxide solution (Alfa Aesar, Ward Hill, Mass.), were of analytical grade and used without any further purification. All solutions were prepared using deionized water (Millipore) as the solvent.

Figure 5:
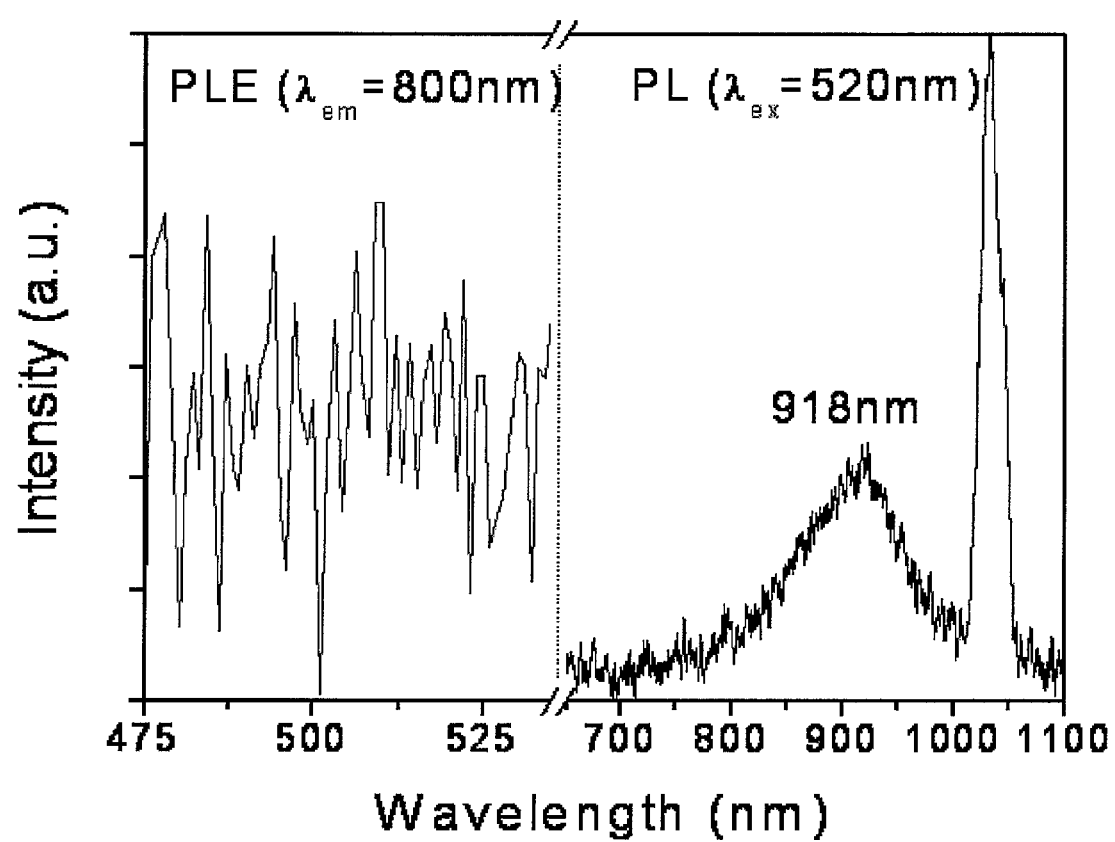
FIG. 5 is a photoluminescence excitation and emission spectra of $Cd_{0.3}Pb_{0.7}S$ QD with a MPA:(Cd+Pb):S molar ratio of about 2:3:1.

The process for synthesizing quantum dots, such as $Cd_{0.3}Pb_{0.7}S$, involved mixing 14 μl MPA with about 38 ml DI $H_2O$ while stirring. The MPA acts as a capping molecule for the eventually synthesized quantum dots. The cations were added to the solution at a reduced rate. The controlled addition of cations was achieved using a peristaltic pump; the preferred rate at which 0.6 ml of 0.04 M $Cd(NO_3)_2$ and 1.4 ml of 0.04 M $Pb(NO_3)_2$ were introduced to the solution was about 0.13 to about 0.18 ml/min. By adding the cations to the solution at a reduced rate, it was possible to control and limit the size of the quantum dots. Once the cations were completely added, the solution was mixed for five minutes. At this point, the solution turned a milky white. An adequate amount of base, 1 M tetrapropylammonium hydroxide solution was then added to raise the pH of the solution to about 9. After allowing the solution to mix another five minutes, 4 ml of about 0.02 M $Na_2S$ precursor was quickly added to the solution all at once turning the solution a darker brown color. After five minutes, an excess 4 ml of 0.04 M $Cd(NO_3)_2$ was added very slowly by hand, causing the solution to become a bit cloudy. After waiting ten minutes to allow the quantum dots to aggregate, 1 M tetrapropylammonium hydroxide solution was added to raise the pH of the solution to about 12. At this point, the solution cleared up a bit. The resulting quantum dot solution had an MPA:(Cd+Pb):S molar ratio of about 2:3:1 and a total volume of about 50 ml. FIG. 5 is a fluorescence spectrum of the quantum dots showing a well defined NIR emission peak at about 918 nm.

Example 6

Exemplary aqueous $Zn_{0.2}Pb_{0.8}S$ quantum dots were synthesized at room temperature according to the following procedure. Precursor solutions of zinc nitrate ($Zn(NO_3)_2.6H_2O$), lead nitrate ($Pb(NO_3)_2$), and sodium sulfide ($Na_2S.9H_2O$) were dissolved in deionized (DI) water at 0.08 M concentrations without prior chemical purification. A solution of MPA:$Zn_{0.2}Pb_{0.8}$:S having a molar ratio of about 2:1:1 was synthesized for a final volume of about 50 ml with a nominal concentration of about 0.4 mM based on the concentration of S.

Figure 6:
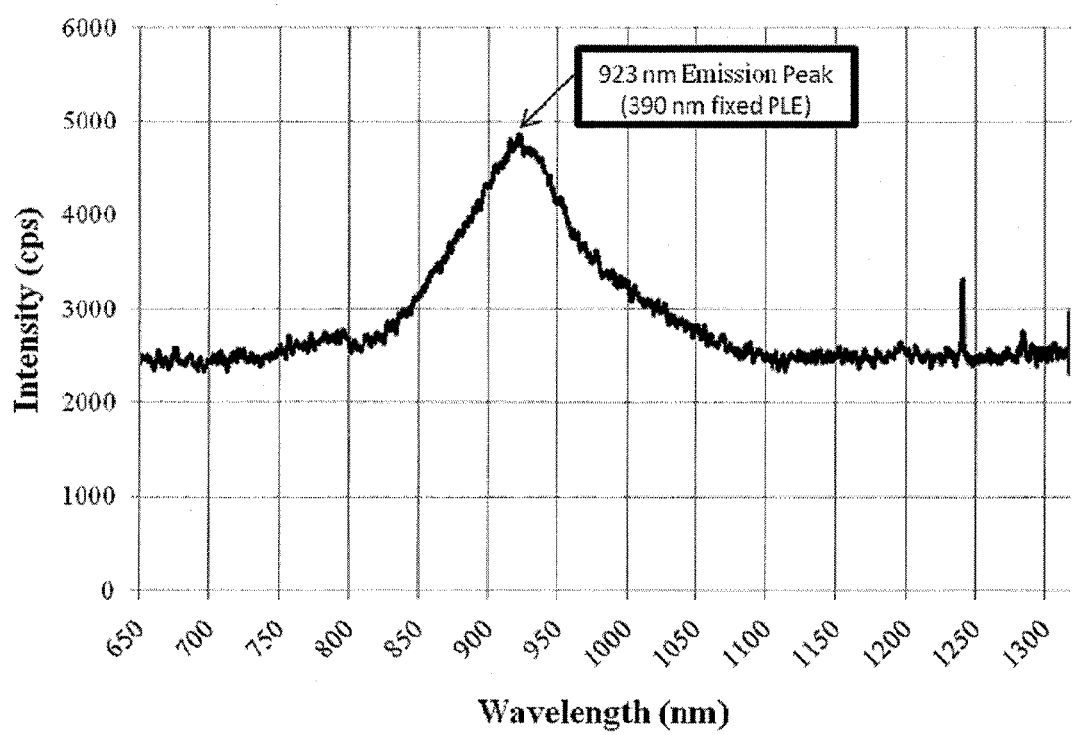
FIG. 6 is an emission spectra for MPA capped $Zn_{0.2}Pb_{0.8}S$ quantum dots with a MPA:ZnPb:S molar ratio of about 2:1:1 at total sulfur concentration of 0.4 mM, wherein the excitation wavelength was fixed at 390 nm.

The solution was produced by first dissolving 3.5 μl of 11.475 M 3-mercaptopropionic acid (MPA) while maintaining a pH of about 12 with the alkaline agent 1M tetrapropylammonium hydroxide (TPAH). 50 μl of Zn ion precursor and 200 μl of Pb ion precursor were then added to the MPA solution under continuous stirring while maintaining a pH of about 12 throughout. A sulfide ion precursor was then rapidly added to the solution under vigorous stirring to produce 80% Pb doped ZnS quantum dots with 5 minutes of additional stir time. A fixed excitation wavelength of 390 nm was delivered to the quantum dots using a QM-4/2005 spectrofluorometer by PTI at maximum intensity (slit width of 6 mm for 24 nm bandpass using 1200 lines/mm grating). As shown in FIG. 6, the photoluminescence spectra of the quantum dots were measured on an Ocean Optics USB4000 revealing an emission peak at about 923 nm.

Figure 7:
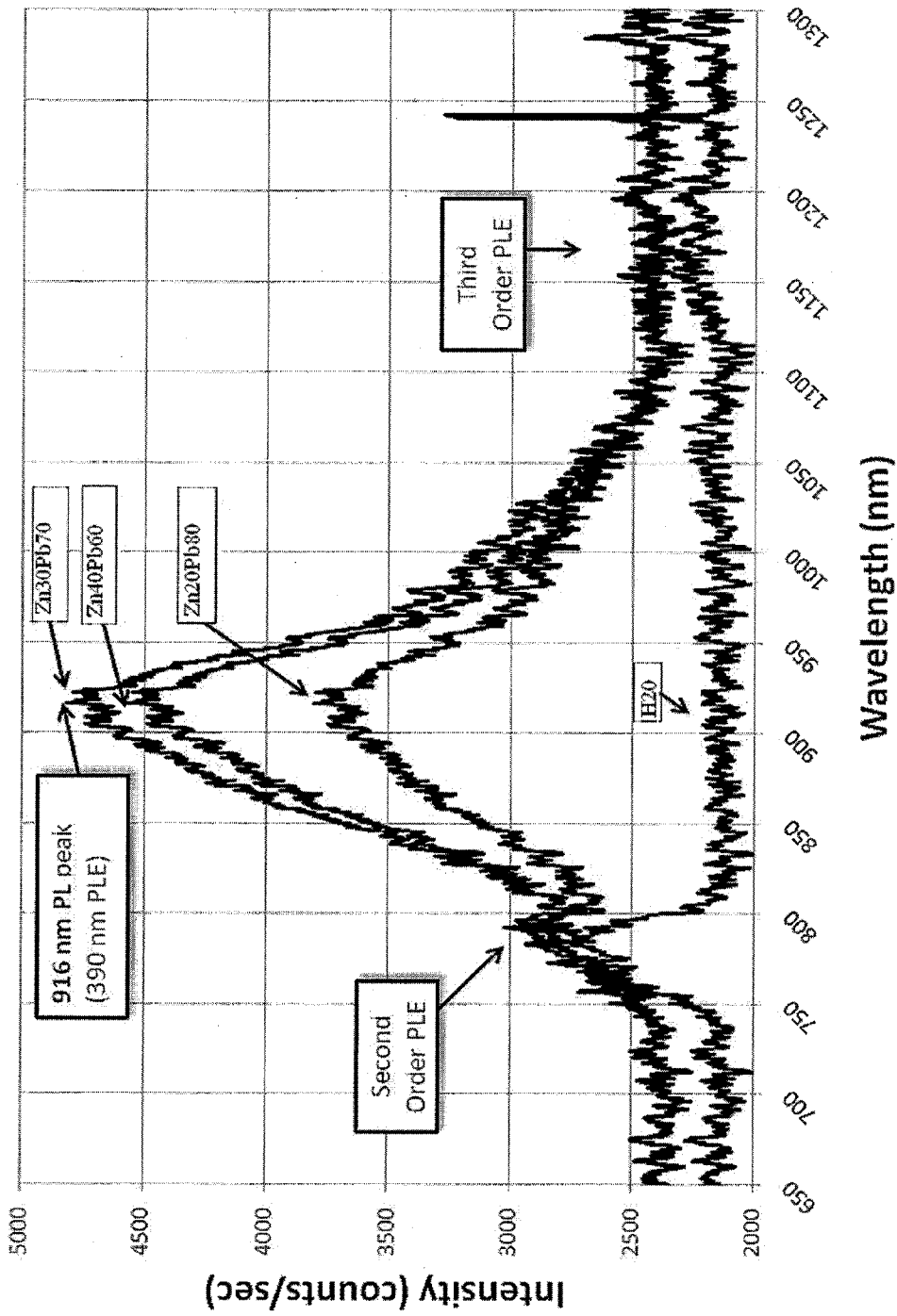
FIG. 7 is an emission spectra for MPA capped $Zn_xPb_{(1-x)}S$ quantum dots with a MPA:ZnPb:S molar ratio of about 2:1:1 at a total sulfur concentration of 0.4 mM, wherein the excitation wavelength was fixed at 390 nm.

FIG. 7 shows the photoluminescence emission spectra for lead doped zinc sulfide quantum dots at varying doping levels following the experimental procedures outlined above. The only procedural change occurred when the Zn to Pb ratios of the precursor solutions were adjusted to accommodate different Pb doping levels. The final sulfur concentration for the samples was fixed at 0.4 mM while excited at a fixed photoluminescence excitation (PLE) of 390 nm for all samples. The samples received a long exposure time of approximately 10 minutes on the USB 4000 NIR detector. These results confirmed the earlier synthesis of NIR quantum dots having a doping level of 80% Pb. The 60%, 70%, and 80% Pb doped samples in FIG. 7 show that there exists a Pb-rich solid phase that is formed upon doping ZnS quantum dots. This explains why there was an absence of a blue or red shift for the different doping levels, with all samples sharing an emission (PL) peak about 916 nm. The 70% Pb doped sample exhibited the highest intensity levels.

Figure 8:
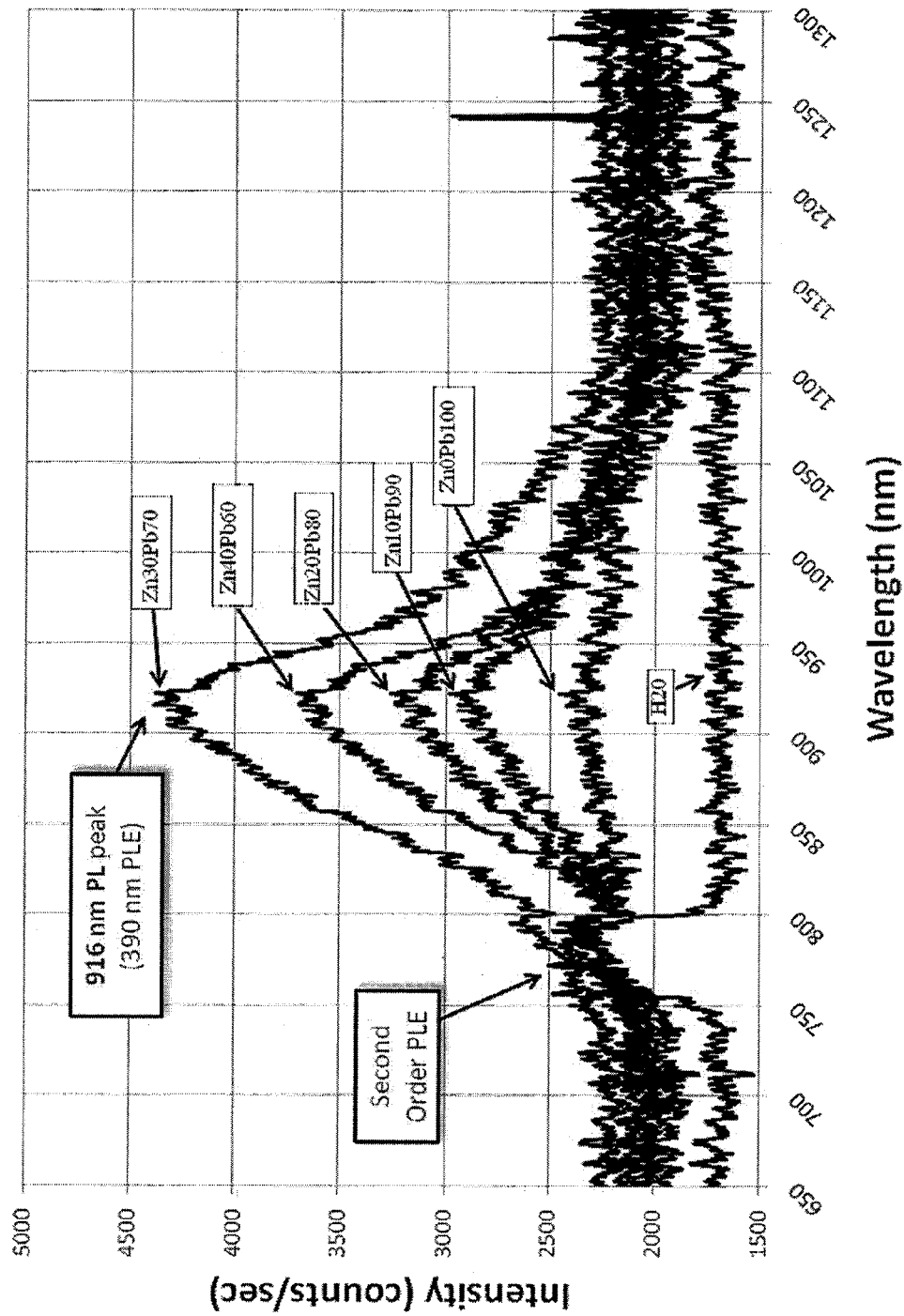
FIG. 8 is an emission spectra for MPA capped $Zn_{1-x}Pb_xS$ quantum dots with a MPA:ZnPb:S molar ratio of 2:1:1 at a total sulfur concentration of 0.4 mM.

To better understand the Pb-rich region, Pb doping levels were taken up to 100% Pb without any Zn precursor added to solution. FIG. 8 shows the results of these high Pb doping levels, and includes pure PbS (100% Pb doped), wherein the excitation wavelength was fixed at 390 nm. These steps were taken since pure PbS creates dark suspensions, where lower final concentrations allow for better transmission of the light source and emission detection. The short exposure time of approximately 1 minute on the USB4000 resulted in inconsistent noise levels for the various samples, but still confirmed the presence of the Pb-rich region. The sample with 70% Pb doping resulted in the highest emission intensity, and that the Pb-rich solid formed in $Zn_{1-x}Pb_xS$ quantum dots occurred from 60% Pb doping up to 90% Pb doping. Pure PbS showed insignificant emission intensity.

The foregoing examples have been presented for the purpose of illustration and description and are not to be construed as limiting the scope of the invention in any way. The scope of the invention is to be determined from the claims appended hereto.

What is claimed is:

1. A quantum dot having the formula $D_xM_{(1-x)}Se_yS_{(1-y)}$;
    where M is a metal selected from the group consisting of cadmium and zinc;
    D is selected from the group consisting of: lead, iron, manganese and mixtures thereof;
    S represents sulfide;
    Se represents selenide;
    wherein y is within the range of 0-1; and
    wherein x is from 0.25 to 0.85 and is selected to provide a quantum dot having an emission having a wavelength of from about 750 nm to about 1100 nm.

2. The quantum dot of claim 1, wherein x is from 0.4-0.8.

3. The quantum dot of claim 1, wherein said quantum dot comprises a sulfide.

4. The quantum dot of claim 1, wherein said quantum dot comprises a selenide.

5. The quantum dot of claim 1, wherein said quantum dot comprises a sulfide selenide.

6. The quantum dot of claim 1, wherein said metal M is zinc.

7. The quantum dot of claim 1, wherein said metal M is cadmium.

8. The quantum dot of claim 1, wherein D is lead.

9. The quantum dot of claim 1, wherein a molar ratio of (D and M):(Se and/or S) is equal to or greater than 1.

10. The quantum dot of claim 9, wherein y is equal to 0.

11. The quantum dot of claim 1, further comprising a capping molecule, wherein a molar ratio of capping molecule:(D and/or M) is from about 1:3 to about 8:1.

12. The quantum dot of claim 11, wherein y is equal to 0.

13. The quantum dot of claim 1, wherein said quantum dot is synthesized according to the method of:
    forming a solution comprising a metal salt and a water-soluble sulfide or selenide;
    precipitating said quantum dot from said solution; and
    subsequently adding cations to a quantum dot core precipitated from said solution.

14. The quantum dot of claim 13, wherein said method for synthesizing said quantum dot further comprises the step of adding said metal salt to said solution over a time period of from about 10 to about 20 minutes.

* * * * *